(12) United States Patent
Stiller et al.

(10) Patent No.: US 8,439,821 B2
(45) Date of Patent: *May 14, 2013

(54) SYSTEM AND METHOD FOR THE CENTRAL CONTROL OF DEVICES USED DURING AN OPERATION

(75) Inventors: Heinz-Werner Stiller, Jestetten (DE); Pavel Novak, Stetten (CH); Klaus M. Irion, Emmingen-Liptingen (DE)

(73) Assignee: Storz Endoskop GmbH (CH)

( * ) Notice: Subject to any disclaimer, the term of this patent is extended or adjusted under 35 U.S.C. 154(b) by 703 days.

This patent is subject to a terminal disclaimer.

(21) Appl. No.: 12/364,328

(22) Filed: Feb. 2, 2009

(65) Prior Publication Data

US 2009/0143644 A1    Jun. 4, 2009

Related U.S. Application Data

(60) Division of application No. 10/379,152, filed on Mar. 4, 2003, now Pat. No. 7,485,114, which is a continuation of application No. PCT/EP01/10189, filed on Sep. 5, 2001.

(30) Foreign Application Priority Data

Sep. 5, 2000   (EP) .................................... 00119179

(51) Int. Cl.
| | |
|---|---|
| *A61B 1/00* | (2006.01) |
| *A61B 17/00* | (2006.01) |
| *A61B 1/04* | (2006.01) |
| *G05B 15/02* | (2006.01) |
| *G05B 11/01* | (2006.01) |
| *G05B 15/00* | (2006.01) |

(52) U.S. Cl.
USPC ........ 600/101; 606/1; 348/72; 700/9; 700/20; 700/83; 128/922

(58) Field of Classification Search .................. 600/101, 600/118, 109; 340/825, 3.1, 3.42, 3.43, 3.44, 340/825.19; 606/1, 130; 700/20, 79, 83, 9; 348/72, 348/77; 128/922

See application file for complete search history.

(56) References Cited

U.S. PATENT DOCUMENTS

| | | | |
|---|---|---|---|
| 4,611,291 A | | 9/1986 | Hoelscher |
| 5,159,446 A | * | 10/1992 | Hibino et al. .................. 348/65 |

(Continued)

FOREIGN PATENT DOCUMENTS

| | | |
|---|---|---|
| DE | 19904090 A1 | 8/2000 |
| EP | 0747279 A1 | 12/1996 |
| WO | 9921165 A1 | 4/1999 |

OTHER PUBLICATIONS

International Search Report; PCT/EP01/10189; Aug. 20, 2002; 3 pages.

*Primary Examiner* — Kevin C Sirmons
*Assistant Examiner* — Bradley G Thomas, Jr.
(74) *Attorney, Agent, or Firm* — St. Onge Steward Johnston & Reens LLC

(57) ABSTRACT

The present invention relates to a system for the central control of devices used during an operation, comprising a first control unit for control of said devices. The system is characterized in that a second control unit is provided which is connected to the first control unit for exchange of information. The first control unit may be embodied as closed system for control of at least those devices which carry out safety-related functions (safety-related devices), and the second control unit may be embodied as open system for control of the remaining devices which carry out non safety-related functions (non safety-related devices). The invention further relates to a method for the central control of devices.

11 Claims, 1 Drawing Sheet

U.S. PATENT DOCUMENTS

| | | |
|---|---|---|
| 5,339,261 A | 8/1994 | Adelson et al. |
| 5,553,237 A | 9/1996 | Eisenberg et al. |
| 5,561,767 A | 10/1996 | Eisenberg et al. |
| 5,572,999 A | 11/1996 | Funda et al. |
| 5,622,528 A * | 4/1997 | Hamano et al. ............... 600/118 |
| 5,627,584 A * | 5/1997 | Nishikori et al. ............... 348/72 |
| 5,788,688 A | 8/1998 | Bauer et al. |
| 5,819,229 A | 10/1998 | Boppe |
| 6,120,435 A | 9/2000 | Eino |
| 6,347,252 B1 | 2/2002 | Behr et al. |
| 6,480,762 B1 * | 11/2002 | Uchikubo et al. ............ 700/253 |
| 6,581,117 B1 * | 6/2003 | Klein et al. ................... 710/110 |
| 6,602,185 B1 * | 8/2003 | Uchikubo .................... 600/118 |
| 6,642,836 B1 | 11/2003 | Wang et al. |
| 6,911,916 B1 * | 6/2005 | Wang et al. ................... 340/3.7 |

* cited by examiner

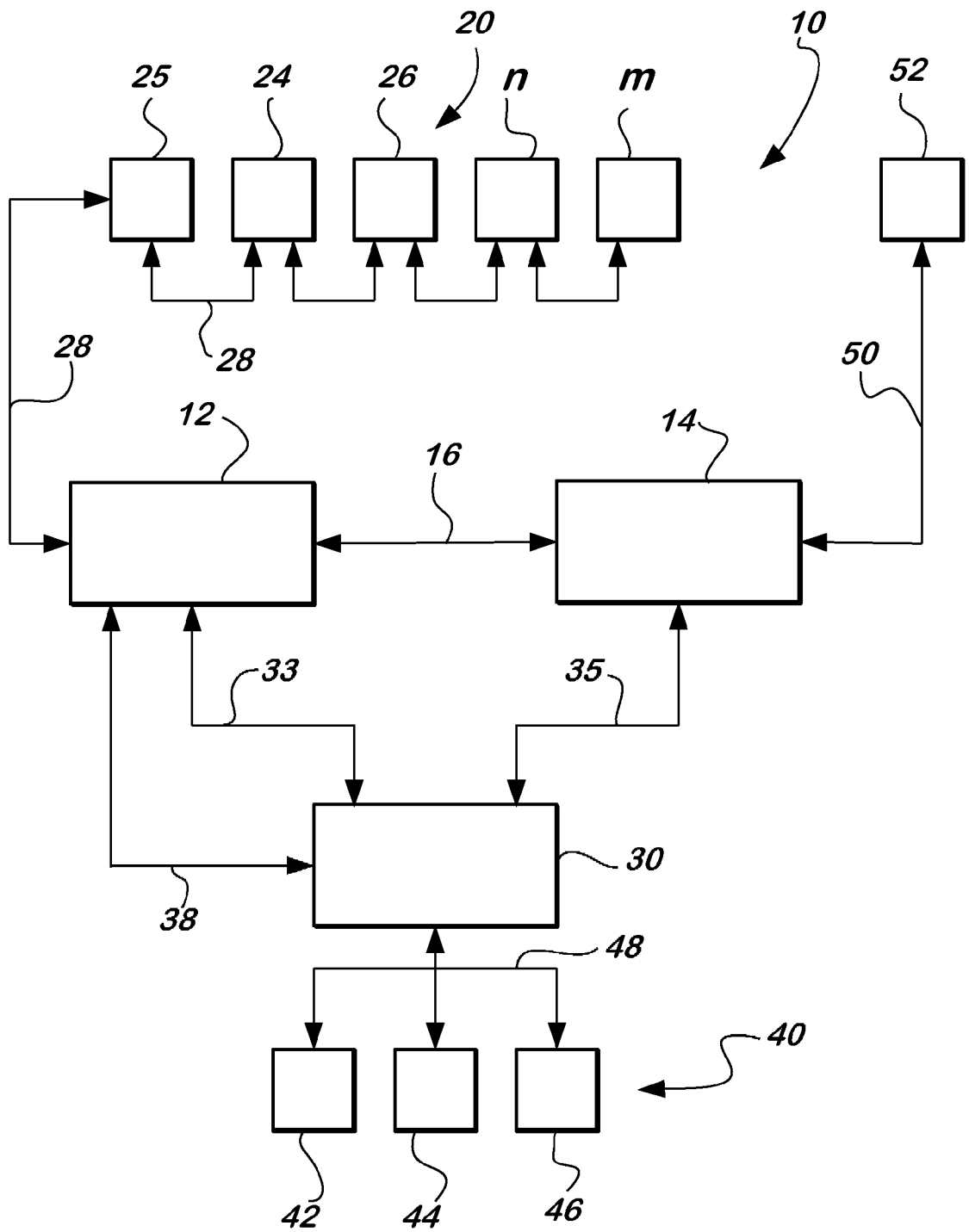

SYSTEM AND METHOD FOR THE CENTRAL CONTROL OF DEVICES USED DURING AN OPERATION

CROSS-REFERENCE TO RELATED APPLICATIONS

This application is a divisional application of U.S. patent application Ser. No. 10/379,152 filed Mar. 4, 2003 now U.S. Pat. No. 7,485,114, which in turn is a continuation of international patent application PCT/EP01/10189 filed Sep. 5, 2001 and designating the U.S., which claims priority of European Application EP 00 119 179.0, filed Sep. 5, 2000.

FIELD OF THE INVENTION

The present invention relates to a system and a method for the central control of devices, particularly medical devices, which are used during an operation. Specifically, the invention relates to a system controlled by first and second controllers in communication with each other.

BACKGROUND OF THE INVENTION

For ergonomic reasons it is desirable to be able to remote control and control, respectively, the control device of all systems required during an operation from a central position, if possible out of a sterile area. Such a control may be carried out for example via a touch-screen (with a sterile cover) or via a voice control. The controlled devices and systems, respectively, may comprise for example endoscopic devices, as well as an op-table, op-lighting, room lighting, air conditioning, telephone, pager, internet, hospital-information system, consumption parts, management system and so on.

In view of the control of medical devices document DE 199 04 090 A1 for example discloses to interconnect single devices via a CAN-bus, the single devices being used as slaves and a host computer as master. All devices are controllable via this host computer.

The disadvantage of such a network is for example that the software- and hardware-efforts to be taken for the single host computer are very high since it has to be adapted to the device to be controlled having to fulfill the highest safety requirements. In view of devices to be controlled without having to fulfill these high safety requirements it may be possible that flexibility and simplicity of the handling may be lost.

If the single host computer is designed by applying a less stringent standard with respect to safety aspects, the risk would arise (for example for a PC with standard software like Windows-NT), however, said safety-related functions would be endangered by unreliable functions of non safety-related systems.

In this case it is assumed that the mentioned medical devices may be divided into two different groups, namely safety-related systems on the one hand, as for example endoscopic devices (insufflators, pumps, or RF-surgery and so on), op-table-control etc., namely devices or systems which may be life-threatening for a patient in the event of a breakdown or failure, and non-safety-related systems on the other hand, like picture archiving, material management systems, telephone remote control etc.

SUMMARY OF THE INVENTION

In view of the above the object of the present invention is to provide for a system and a method, respectively, which do not have the before mentioned disadvantages. Particularly it is to increase the safety in respect to the control of safety-related devices.

This object is solved by the system of the afore-mentioned kind by providing a second control unit which is connected with the first control unit for exchange of information, and the first control unit is embodied as a closed system for control of at least those devices which carry out safety-related functions (safety-related devices) and the second control unit is embodied as an open system for control of the remaining devices which carry out non safety-related functions (not safety-related devices).

This means in other words that the inventive system does not use a single host computer at has been done up to now, but uses two control units instead which are each assigned to different groups of devices to be controlled. When assigning the devices to be controlled to those control units it is assumed that there are generally devices for carrying out safety-related functions (for example endoscopic devices) and on the other hand devices for carrying out non-safety-related functions, like room lightening, air conditioning etc., during an operation. In this connection the term "closed system" describes a system which does not allow any intervention from outside the system.

Such a system cannot be manipulated, reconfigured etc. neither by a user directly nor via the internet etc. In contrast thereto an open system may be configured or for example supplemented by a user. Here, interventions and manipulations, respectively, from outside are possible.

The advantage of the inventive system is among others that the provision of a further control unit increases the safety with respect to undesired erroneous or faulty functions without limiting the flexibility of the whole system thereby. Due to the fact that on the second control unit software may be used which have not to fulfill such stringent safety requirements as it is the case for the control of safety-related devices, standard software may be used so that the single investment costs on the one hand as well as the running maintenance costs of the total system on the other hand may be reduced.

A further advantage of the inventive system is that the first control unit which is responsible for the control of the safety-related devices is embodied as a closed system which secures that all attempts to manipulate the operating system are disabled. Moreover also manipulations of the applications for controlling the safety-related devices are impossible.

At this point it is to be noted, however, that on the first control unit also applications for control of non safety-related devices could run provided that these applications have been tested under safety aspects before.

Advantageously, those control units are each part of independent computers (PC's). Of course, it is also contemplated that those control units are integrated in one computer which comprises at least two processors (CPU) with one control unit being realized by one processor.

When using a single host computer and considering such requirements it would not be possible to carry out the control of non safety-related devices with the desired simplicity and flexibility. Moreover the risk would always arise that erroneously programmed software for the non safety-related devices would influence the control of safety-related devices.

In a preferred embodiment the first control unit and the safety-related devices are interconnected via a bus-system preferably the Karl Storz-communication-bus (SCB®). Preferably, the non safety-related devices and the second control unit are interconnected via a further bus-system, both bus-systems preferably being different.

These measures result in a simplification of the system as well as to a reduction of the total costs since the especially designed bus-system for safety-related functions is not used for the control of every device. Rather also conventional standard bus-systems may be used. Hence the expensive safety bus-system is only used for the interconnection of the safety-related devices.

In a preferred embodiment an interface unit is provided which is connected with both control units on the one hand and with peripheral devices on the other hand and which connects each of the control units with the peripheral devices. Preferably, the interface unit is controlled by the first control unit via a control line. More preferably the peripheral devices comprise a monitor device and/or an input device, preferably a keyboard and a mouse. More preferably, the monitor device is provided as a touch-screen also allowing an input.

These above mentioned measures result in the advantage that the costs for the total system are reduced on the one hand and the handling is significantly simplified on the other hand since the peripheral devices required for input of control instructions or for monitoring of parameters are provided only once. The surgeon has not to observe plural monitor devices hence. Further, the control line between the interface unit and the first control unit guarantees that the control unit controlling the important safety-related devices also allows the respective necessary function and displays the important safety-related parameters on the touch-screen in case of a breakdown and an failure, respectively, of the second control unit. Altogether, also an increase of the safety level of the system is achieved.

In a preferred embodiment the second control unit comprises a receiving means to capture error messages from the first control unit and to display them on one of the peripheral devices.

This measure has the advantage that also in case of a connection of the second control unit with the interface unit for the control of non safety-related devices error messages concerning safety-related devices are immediately provided to the user of the system. It may hence be avoided that the display of such error messages is only signaled to the user upon re-switching the connection from the first control unit to the peripheral devices. Consequently, this has the advantage that the safety of the total system is further increased.

Preferably the safety-related devices include endoscopic devices, preferably insufflators, pumps, light sources, video devices and for example op-table-controllers etc. The non safety-related devices include for example picture archiving, op-lighting, room lighting, telephone, air conditioning, pager, internet, hospital system, consumption parts, management systems, etc.

It is further preferred to interconnect both control units via an Ethernet-bus (TCP/IP-protocol), since this type of bus-system has been proved as reliable and cost effective.

In a preferred embodiment the first control unit comprises an embedded operating system, preferably "embedded windows NT", which is protected against interventions from outside the system.

This means in other words that the operating system of the first control unit is a fixed component of the unit and is hence protected against manipulations. The user may not carry out any interventions into the operating system. This would be possible for example with current PC's. Hence, it is avoided that specific safety-related functions cannot be carried out anymore or are carried out erroneously due to intentional or unintentional interventions into the operating system.

In a preferred embodiment the first control unit comprises a check means which cyclically checks the connection with the interface unit and outputs an error message if a connection is not present.

Also this measure results in an increase of safety because the system signalizes the user immediately when a display and a setup, respectively, of respective parameters of safety-related devices are not possible anymore due to the failure of the interface unit.

In a preferred embodiment the first control unit comprises a voice control, for example in form of a software module.

This measure has the advantage that the operation by the surgeon is simplified.

The object underlying the present invention is also solved by a method for the central control of devices used during an operation in that the devices for the control of safety-related functions are controlled by a first control unit and the devices for carrying out non safety-related functions are controlled by a second control unit.

This method allows one to realize the advantages mentioned in connection with the afore-mentioned inventive system in the same manner so that the advantages may not be described here anymore.

In a preferred embodiment both control units communicate with each other, while preferably the first control unit checks the second control unit for faults. It is further preferred to provide for an interface unit which is controlled by the first control unit and which in response thereto forwards signals either from the first or the second control unit to a common peripheral device.

This measure has—as already mentioned—the advantage that the costs of the system are reduced and the ease of operation is increased.

In a preferred embodiment the first control unit will drive the interface unit in case of a failure of the second control unit such that the signals of the first control unit are forwarded to the peripheral devices.

This means in other words that the first control unit ensures that a failure in the second control unit does not result in the breakdown of the connection between the first control unit and the peripheral devices.

In a preferred embodiment the interface unit forwards the signals of the first control unit to the peripheral devices immediately if a safety-related function is to be carried out.

This measure has the advantage that the important functions are possible also when the present connection between the second control unit and the peripheral devices is present. The result is an increase of safety.

In a preferred embodiment the interface unit forwards the signals of the second control unit to the peripheral devices after activating a non safety-related function only when the safety-related function is completed and completely carried out, respectively. This means in other words that the execution of safety-related functions cannot be interrupted by switching the interface unit. Rather, the execution of the safety-related function is carried out up to the end and only than the interface unit will build up the connection between the second control unit and the peripheral devices.

Further advantages and embodiments of the invention can be taken from the following description and the enclosed drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

FIG. 1 shows a schematic block diagram of a system for the central control of devices used during an operation in accordance with the invention.

DETAILED DESCRIPTION OF THE INVENTION

In the FIGURE a system for the central control of devices used during an operation is shown as a block diagram and is indicated with reference numeral 10. The system 10 comprises a first computer unit 12 and a second computer unit 14. Both computer units 12, 14 are interconnected via a bus-connection 16, for example an Ethernet-bus-connection, in order to exchange data in form of messages.

Both computer units 12, 14 are provided as medical PC's, wherein the first computer unit 12 uses an embedded operating system, preferably an "embedded windows NT"-operating system. The second computer unit 14 operates preferably with a common windows operating system or another non-embedded operating system.

The first computer unit 12 serves at least for the control of medical devices, which carry out safety-related and safety critical functions, respectively. In the FIGURE, these safety-related devices are indicated with reference numeral 20. For example, in the FIGURE, a pump 25, an insufflator 24 and RF generator 26 are shown. This exemplary enumeration of three devices is not to be understood in any limiting sense what is indicated in the FIGURE by further devices n and m. Furthermore, the first computer unit 12 may also be used for the control of non safety-related devices provided that respective tested software is used. However, this possibility will not be further discussed below.

The communication between the first computer unit 12 and the safety-related devices 20 is achieved via a bus-system 28 which allows a safe transmission of data. In view of this bus-system 28 other requirements with respect to fail safety has to be considered as is the case in the afore-mentioned Ethernet-bus 16. The applicant offers such a bus-system for example under the name Karl Storz-Communication-Bus (SCB®).

The system 10 further comprises a switching unit 30. The switching unit 30 is connected with its input side to the computer unit 12 and the computer unit 14, wherein in the FIGURE only one connection line 33, 35 each is exemplarily shown. It is to be understood that these connection lines 33, 35 comprise a plurality of single connection lines.

On the output side the switching unit 30 is connected with peripheral devices 40, wherein in the FIGURE a touch sensitive monitor 42 (called touch-screen), an input keyboard 44 as well as a mouse 46 are shown as an example. The peripheral devices 40 are located for example in the direct sphere of the surgeon in the operation room so that these peripheral devices 40 have to be adapted accordingly. The touch-screen 42 is for example provided with a sterile cover.

The connection of the peripheral devices 40 with the switching unit 30 is made via respective lines 48, wherein for simplification reasons only one line is shown each representing a plurality of connecting lines.

A switching unit 30 has the task to connect each peripheral device 42 to 46 with one of both computer units 12, 14 so that the input and the display, respectively, of data is possible.

The control of the switching unit 30 is provided by the first computer unit 12, and respective control signals may be transmitted to the switching unit 30 via a control line 38.

The second computer unit 14 is connected (indirect-coupled) with the devices 52 via an optical bus 50, which devices carry out non safety-related functions. Such functions are for example telephone remote control, room lighting, etc. The control of these non safety-related devices is hence achieved by the second computer unit 14.

As already mentioned, the first computer unit 12 is equipped with an embedded operating system. This should guarantee that interventions into the systems or manipulations of the systems from outside are not possible. The first computer unit 12 is embodied as a closed system on which only tasks are running which are required for the control of the safety-related devices 20. Also, tasks may run additionally which serve to control the non safety-related devices 42 in case that these tasks are tested in view of safety aspects before.

The second computer unit 14 is however provided as a common medical PC. In contrast to the first computer unit 12 no tasks are allowed to run on the second computer unit 14, which tasks serve to control safety-related devices.

Both computer units 12, 14 supply data by the respective lines 33, 35 to the switching unit 30 and depending on the "position" of the switching unit only the data of one of both computer units are displayed on the touch-screen 42. Also the input of data is carried out only in this computer unit. In case that the surgeon wants to select for example functions of the other group of devices, he may do this via a respective input of an instruction which is either directly received by the first computer unit 12 or indirectly received via the computer unit 14 and the bus 16 by the first computer unit 12. In response thereto it transmits a respective control signal via the control line 38 causing a switching in the switching unit 30. On the touch-screen 42 the respective data, selecting menus etc. of the selected group of devices will then be displayed.

In case of a connection between the second computer unit 14 with the peripheral devices 40 it is necessary that any error messages relating to safety-related devices 20 are immediately signalized to the surgeon independent of the switch condition of the switching unit 30 via the touch-screen 42. For this, a task is running in the second computer unit 14 which continuously checks the messages sent by the first computer unit 12 via the bus 16 for failure messages. If an error message is detected the second computer unit 14 ensures that a window is opened on the touch-screen in which the error message is displayed.

A further task of the first computer unit 12 is to check the presence of the switching unit 30. If the switching unit 30 cannot be detected anymore by the first computer unit 12 for example due to breakdown, the first computer unit 12 must immediately generate an error message. This error message is to signalize the surgeon that an appropriate display and an input of data via the peripheral devices 40 may not be guaranteed anymore.

Further it is necessary that the first computer unit 12 checks the second computer unit 14 and in case of a failure the switching unit 30 is immediately set in those switching conditions in which the first computer unit 12 is connected with the peripheral devices 40.

Under safety aspects it is also necessary that when inputting an instruction for switching the peripheral devices 40 to the second computer unit 14 all not yet completed functions of the safety-related devices 20 are first completed with a respective display of the parameters. This is to guarantee that the execution of these safety-related functions is not terminated to early. In the reverse case, however the peripheral devices 40 are immediately connected with the first computer unit 12 so that a safety-related function may be carried out without any delay.

It is to be understood that the invention may be realized not only in form of the afore-mentioned embodiment but also in other embodiments. The scope of such modifications is only defined by the appended claims.

What is claimed is:

1. A system for controlling medical devices, comprising:
   a first controller;
   at least one medical device having safety-related functions controlled by said first controller;
   a second controller in communication with said first controller;
   at least one device having non-safety-related functions controlled by said second controller;
   wherein said second controller can only control devices that do not have safety-related functions;
   a touch panel that communicates a control command associated with said at least one medical device having safety-related functions and a control command associated with said at least one device having non-safety related functions to said second controller;
   wherein said second controller controls said at least one device having non-safety-related functions based on the control command associated therewith received from said touch panel; and
   wherein said second controller communicates the control command associated with said at least one medical device having safety related functions received from said touch panel to said first controller.

2. The system of claim 1, wherein said first controller further controls at least one device having non-safety-related functions.

3. The system of claim 1, wherein said first controller includes embedded operating system software executing thereon.

4. The system of claim 1, wherein said at least one device having safety-related functions includes devices for communicating medical imaging data.

5. The system of claim 4, wherein said at least one device for communicating medical imaging data comprises an endoscopic camera for acquiring images.

6. The system of claim 5, wherein said at least one device for communicating medical imaging data further comprises a monitor for displaying images.

7. The system of claim 6, wherein said at least one device having non-safety-related functions includes an image archiving device.

8. The system of claim 1, wherein said first controller includes voice control software executing thereon.

9. The system of claim 1, wherein said first controller is connected to said second controller via an ethernet bus.

10. A method for controlling medical devices, comprising:
    connecting a first controller to at least one medical device having safety-related functions;
    connecting a second controller to at least one device having non-safety-related functions;
    connecting the first controller to the second controller;
    using a touch panel to communicate a control command associated with the at least one device having non-safety related functions to the second controller;
    using the touch panel to communicate a control command associated with the at least one medical device having safety-related functions to the second controller;
    wherein said second controller can only control devices that do not have safety-related functions, and controls the at least one device having non-safety-related functions based on the control command associated therewith received from the touch panel; and
    wherein said second controller communicates the control command associated with the at least one medical device having safety-related functions received from the touch panel to said first controller.

11. The method of claim 10, wherein said first controller includes voice control software executing thereon, further comprising using a microphone to communicate a control command associated with the at least one medical device having safety-related functions to the first controller.

* * * * *